United States Patent [19]
Fell et al.

[11] Patent Number: 5,387,187
[45] Date of Patent: Feb. 7, 1995

[54] RED CELL APHERESIS METHOD

[75] Inventors: Claude Fell, Nyon, Switzerland; Jean Papillon, Germaine-en-laye, France

[73] Assignee: Haemonetics Corporation, Braintree, Mass.

[21] Appl. No.: 203,884

[22] Filed: Mar. 1, 1994

Related U.S. Application Data

[63] Continuation of Ser. No. 984,029, Dec. 1, 1992, abandoned.

[51] Int. Cl.[6] .......................................... A61M 37/00
[52] U.S. Cl. .......................................... 604/6; 604/4; 604/5; 210/782
[58] Field of Search .................. 604/4, 5, 6; 210/782, 210/787, 789

[56] References Cited

U.S. PATENT DOCUMENTS

| | | | |
|---|---|---|---|
| 3,489,145 | 1/1970 | Judson et al. | 128/214 |
| 4,086,924 | 5/1978 | Latham, Jr. | 128/214 R |
| 4,197,847 | 4/1980 | Djerassi | 128/214 R |
| 4,464,167 | 9/1984 | Schoendorfer et al. | 604/6 |
| 4,680,025 | 7/1987 | Kruger et al. | 604/6 |
| 4,850,995 | 7/1989 | Tie et al. | 604/6 |
| 5,135,667 | 8/1992 | Schoendorfer | 210/782 |

FOREIGN PATENT DOCUMENTS

| | | |
|---|---|---|
| 0128683 | 12/1984 | European Pat. Off. . |
| 0171749 | 2/1986 | European Pat. Off. . |
| 0208061 | 1/1987 | European Pat. Off. . |
| WO90/00059 | 1/1990 | WIPO . |

OTHER PUBLICATIONS

Sadoff, B. J., et al., "Experimental 6 log$_{10}$ white cell-reduction filters for red cells", *Transfusion* 32(2):129–133 (Published 1992).

Elias, M. K., et al., "In vitro evaluation of a high-efficiency leukocyte adherence filter", *Ann. Hemtol.* 63:302–306 (1991).

de Graan-Hentzen, Y. C. E., et al., "Prevention of primary cytomegalovirus infection in patients with hematologic malignancies by intensive white cell depletion of blood products", *Transfusion* 29:757–760 (1989).

Steneker, I. and Biewenga, J., "Histologic and immunohistochemical studies on the preparation of white cell-poor red cell concentrates: the filtration process using three different polyester filters", *Transfusion* 31(1):40–46 (1991).

Angelbeck, J. L., "An Overview of Pall Leukocyte Removal Filter Applications and the Sterile Docking Device", *3rd International Congress World Apheresis Association*, Amsterdam, The Netherlands, Apr. 9, 1990.

Pall Biomedical Products Corporation S-PL100 Brochure Rev A, "Pall PL100 TM Leukocyte Removal Filter for Platelet Transfusion".

*Primary Examiner*—Paul Prebilic
*Attorney, Agent, or Firm*—Cesari and McKenna

[57] ABSTRACT

The present invention provides an apheresis apparatus and method for separating blood. A phlebotomy needle draws anticoagulated whole blood from a donor into a separation chamber. The separation chamber separates plasma from higher density blood components. The plasma is displaced to a plasma collection bag. The separation process is terminated and the higher density blood components remaining in the separation chamber are diluted with saline solution and are returned to the donor via the phlebotomy needle. Anticoagulated whole blood is drawn again from the donor into the separation chamber. The separation chamber again separates plasma from higher density blood components in the separation chamber. The separation process is then terminated and the donor is disconnected. The higher density blood components remaining in the separation chamber are displaced to a bag for collecting higher density blood components and is rejuvenated with additive solution.

13 Claims, 2 Drawing Sheets

RED CELL APHERESIS METHOD

This is a continuation of co-pending application Ser. No. 07/984,029 filed Dec. 1, 1992 now abandoned.

BACKGROUND OF THE INVENTION

Using current methods, 10–12 minutes are required for a donor to donate blood, while 30 minutes or longer are required for a donor to donate plasma or platelets. The population willing to donate through apheresis is much smaller than the blood donation population because of the increased time involved. This has become a problem as the need for plasma or platelets has greatly increased.

Accordingly, there is a continuing need for a combined plasmapheresis/red cell or platelet collection apparatus and method for obtaining standard units of blood components with hematocrit in the 65–70% range which is also capable of collecting volumes of plasma with option of platelets of approximately 400 ml in 20 minutes or less from a single donor.

SUMMARY OF THE INVENTION

The present invention provides a separation chamber having an input and an output port for separating blood components into less dense and more dense components. The output port of the separation chamber is in fluid communication with a first container or containers for receiving a less dense component. The input port is in fluid communication with a second container for receiving more dense components. A phlebotomy needle for withdrawing whole blood from a donor is in fluid communication with a third container containing anticoagulant.

The phlebotomy needle draws whole blood from a donor, the whole blood becoming anticoagulated by mixing with anticoagulant drawn from the third container. The anticoagulated whole blood enters into a separation chamber through the input port. Low density component is separated from higher density components in the separation chamber. The less dense component is displaced through the output part into the first container or containers. The separation process is terminated and the higher density components remaining in the separation chamber are diluted with diluent solution stored in a fourth container. The fourth container is in selective fluid communication with the phlebotomy needle. The diluted higher density components are returned to the donor via the phlebotomy needle.

Whole blood is again drawn from the donor and anticoagulated with anticoagulant from the third container. The anticoagulated whole blood enters the separation chamber and the separation chamber again separates low density component from higher density components. The second separation process is then terminated and the phlebotomy needle is removed from the donor. The higher density components remaining in the separation chamber are displaced to a second container which is in selective fluid communication with the input port of the separation chamber. A fifth container containing a volume of additive solution is in fluid communication with the second container and rejuvenates the higher density components entering the second container with additive solution.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
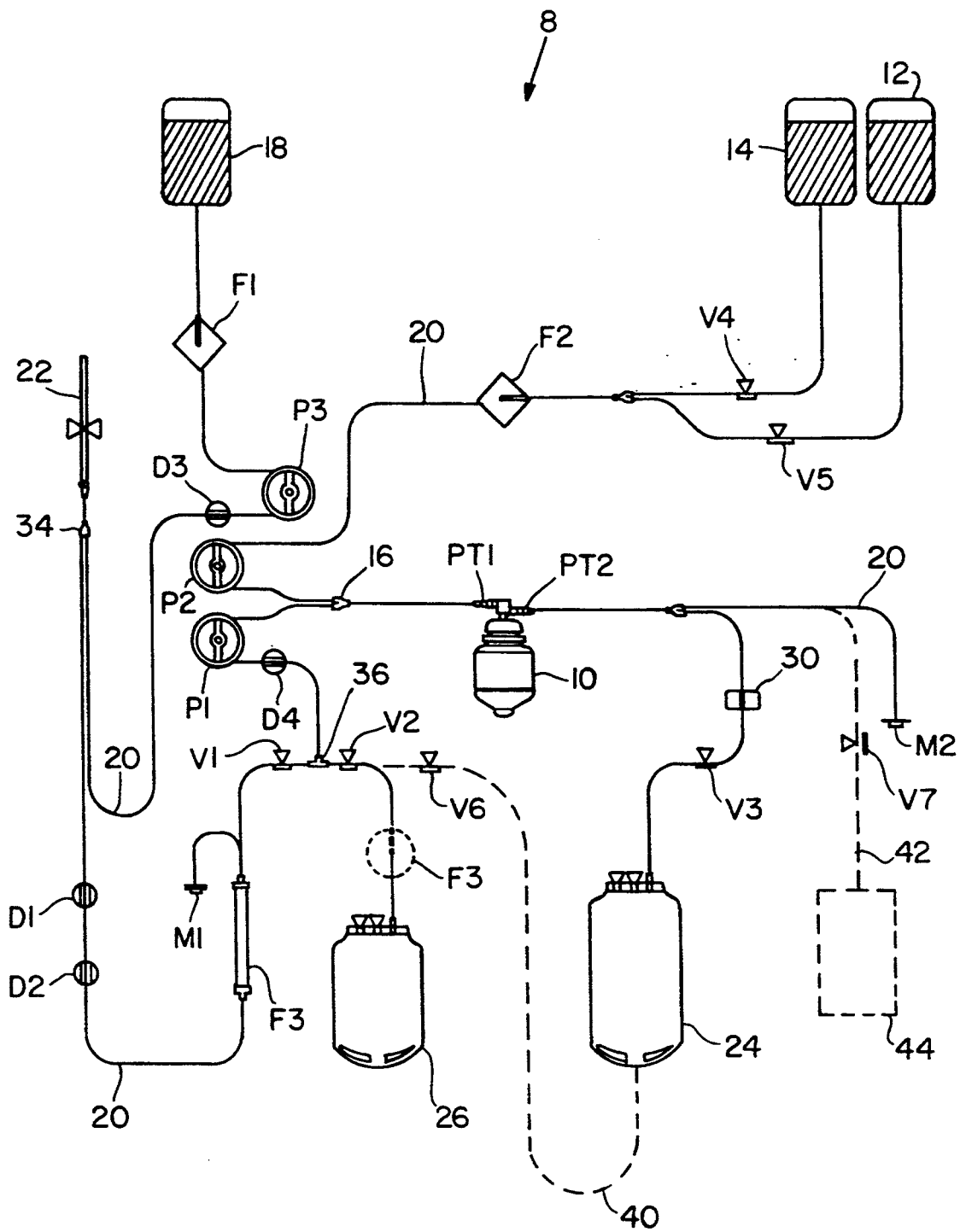
FIG. 1 is a schematic view of the present invention apheresis apparatus.

In FIG. 1, apheresis apparatus 8 uses a standard centrifuge bowl 10 (see U.S. Pat. No. 4,983,158) having an internal fluid capacity of 250 ml. An output port PT2 of centrifuge bowl 10 is in fluid communication with a first container 24 for collecting plasma. An input port PT1 of bowl 10 is selectively coupled through one or more valves V1, V2, V4 and V5 to a phlebotomy needle 22, a second container 26 for collecting red cells, a fourth container 14 for storing saline solution and a fifth container 12 for storing additive or rejuvenating agent. Phlebotomy needle 22 is in fluid communication with a third container 18 containing anticoagulant. The containers are bags made of blood compatible material. The rejuvenating agent is an additive for extending the preservation of red cells such as SAGM, ADSOL and NUTRICELL. Bacterial filters F1 and F2 remove bacteria from solutions drawn from containers 12, 14 and 18. Peristaltic pumps P1, P2 and P3, together with valves V1, V2, V3, V4 and V5 control the direction and duration of flow through blood compatible tubing 20 in response to signals generated, by line sensor 30, donor pressure monitor M1, system pressure monitor M2 and air detectors D1, D2, D3 and D4. Line sensor 30 monitors cells concentration. Air detectors D1, D2, D3, and D4 detect the absence or presence of fluid. Pressure monitors M1 and M2 monitor pressure levels within apparatus 8.

In operation, tubing 20 of apparatus 8 is primed with saline solution from container 14 with valve V1 open, valve V2 closed and pumps P1 and P2 operating. Additionally, valve V4 is open and valve V5 is closed. The saline solution passes through "Y" connector 16 and continues until reaching air detector D4. Air detector D4 detects the presence of saline solution at D4 and terminates the saline solution priming operation. Pumps P1 and P3 prime the tubing 20 of apparatus 8 and needle 22 with anticoagulant solution from container 18. The anticoagulant passes through "Y" connector 34 and continues until reaching air detector D2. Air detector D2 detects the presence of anticoagulant at D2 and terminates the anticoagulant priming operation. Pump P1 then operates drawing the anticoagulant closer to filter F3 through tubing 20 to equalize any pressure created within apparatus 8. Donor pressure monitor M1 and system monitor M2 monitors the pressure within apparatus 8 and terminates the equalizing operation once the pressure is equalized. Equalizing the pressure prevents anticoagulant from being injected into a donor when the phlebotomy needle is inserted. The phlebotomy needle 22 is then inserted within the donor and whole blood is drawn from the donor and mixed with anticoagulant using pumps P1 and P3. Pump P3 mixes anticoagulant from container 18 with the whole blood drawn from the donor. Valve V1 and V3 are open allowing anticoagulated whole blood to be forced into bowl 10 through input port PT1. The ratio of the anticoagulant to whole blood is about 1:16.

Bowl 10 is rotated, and centrifugal forces separate the higher density components, mainly red blood cells from lower density components, i.e. plasma. The red cells are forced to the outer portions of bowl 10 while the plasma remains in the inner portions or the core of bowl 10. The plasma is then displaced from bowl 10 via port PT2 by additional anticoagulated whole blood entering bowl 10 through port PT1. The plasma passes through line sensor 30 and valve V3 before being collected in plasma container 24 where approximately 200-250 ml of plasma is collected. The separation process is then terminated by stopping the rotation of the centrifuge. Pump P1 returns the blood components remaining in bowl 10 to the donor through filter F3 and phlebotomy needle 22 with valve V1 open and Valve V2 closed. Pump P2 mixes saline solution from container 14 with the blood components being returned to the donor with valve V4 open and valve V5 closed. The addition of saline solution to the remaining components allows the components to be returned to the donor at a rapid rate, i.e., 120 ml/sec. At that return rate, the saline solution is introduced by pump P2 at a rate of approximately 60 ml/sec. Alternatively, the contents of the bowl can be diluted and returned with a portion of the donor's plasma. While the contents of the bowl 10 are being returned to the donor, pump P2 primes apparatus 8 with additive solution stored in container 12 up to "Y" connector 16 with valve V4 closed and valve V5 open.

Apparatus 8 then begins a second draw process in which whole blood is again drawn and mixed with anticoagulant. Another 200-250 ml of plasma is separated in bowl 10 and displaced through output port PT2 into plasma container 24. The second centrifugation process is terminated and the phlebotomy needle 22 is removed from the donor. The remaining components in bowl 10 are pumped by pump P1 out of bowl 10 through port PT1. The components are rejuvenated with additive solution drawn from container 12 by pump P2 with valve V4 closed and valve V5 open. As an option, the rejuvenated components can be filtered through leukocyte filter F3 before being collected in red cell container 26 with valve V1 closed and valve V2 open. Filter F3 filters out white blood cells from the diluted components. Filter F3 is then purged, completing the procedure. Alternatively, the contents of the bowl can be collected in container 26 before the additive solution is added. In such a situation, filter F3 is omitted. In a further alternative, additive solution can be preloaded in container 26. In such a case additive container 12 is omitted.

The total procedure time during which a donor is connected is about 18 minutes, as compared to about 10-12 minutes for a standard single draw donation. However, at least 400 ml of plasma is collected in the two draw donation versus 220 ml during a standard single draw donation.

Alternatively, additional collection containers can be added to apparatus 8 in fluid communication with output port PT2 for the collection of platelets and white blood cells. Furthermore, bowl 10 can be a latham type bowl. In order to collect platelets and/or white blood cells, surge line 40 (shown in dotted lines) and valve V6 is added between plasma container 24 and valve V2. Platelet container 44, line 42 and Valve V7 are also added. Surge line 40 allows plasma to recirculate through bowl 10. The recirculating plasma allows platelets to be collected in platelet container 44 as disclosed in U.S. Pat. Nos. 4,416,654 and 4,464,167.

Figure 2:
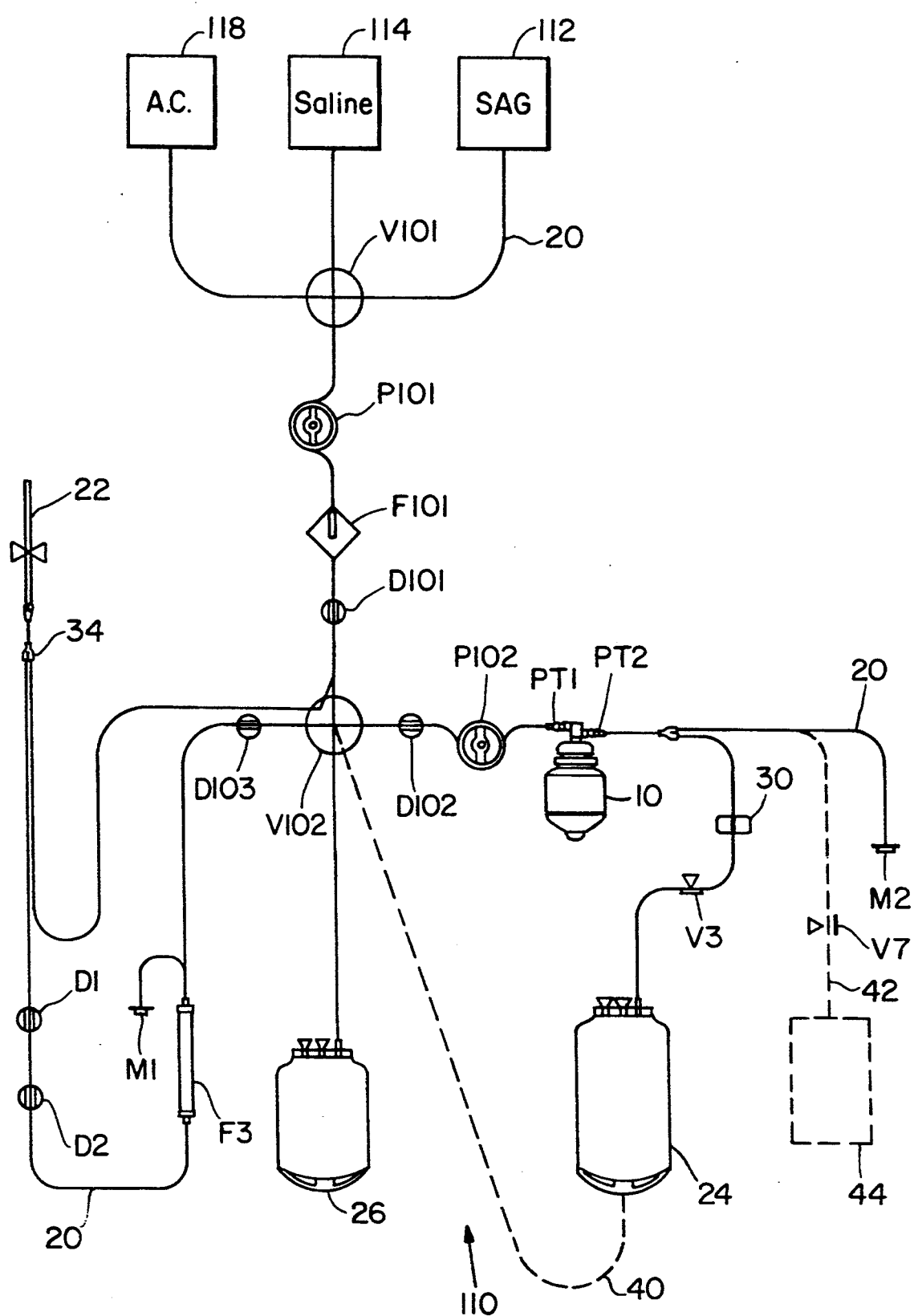
FIG. 2 is a schematic view of another preferred embodiment of the present invention apheresis apparatus.

The apheresis apparatus 110 in FIG. 2 is another preferred embodiment of the present invention. The input port PT1 of bowl 10 having a capacity of 250 ml is selectively coupled through one or more manifold valves V101 and V102 to phlebotomy needle 22 and solution containers 112, 114 and 118. The solution containers contain, respectively, additive solution, saline solution and anticoagulant.

Valves V101 and V102 may comprise multiported disposable valves of the type disclosed in U.S. Pat. No. 4,946,434. Valve V101 selectively couples containers 112, 114 and 118 to valve V102. Valve V102 selectively couples the input port PT1 to container 26, phlebotomy needle 22 and valve V101. Valves V101 and V102 selectively control the direction of fluids flowing within apparatus 110 and are motor activated. Alternatively, valves V101 and V102 can be pneumatically, hydraulically or solenoid activated.

Peristaltic pumps P101 and P102, together with valves V101 and V102 control the direction and duration of flow through blood compatible tubing 20 in response to signals generated, by air detector D1, air detector D2, air detector D101, donor blood level detector D102 and bowl blood level detector D103. Detectors D1, D2, D101, D102 and D103 detect the presence or absence of fluid. A plasma container 24 is coupled to the output port PT2 of bowl 10 and a red cell storage container 26 is selectively coupled via valve V102 to input port PT1. An anti bacterial filter F101 removes any bacteria from solutions drawn from containers 112, 114 and 116.

In operation, pump P101 primes apparatus 110 with saline solution from container 114 through valve V101 until air detector D101 until the detector senses the presence of saline solution at D101 and terminates the saline solution priming operation. Similarly pump P101 primes apparatus 110 with anticoagulant from container 118 through "Y" connector 34 until air detector D2 senses the measure of fluid. The anticoagulant passes through valve V101, pump 101, filter F101, and valve V102 before reaching "Y" connector 34. Detector D2 detects the presence of anticoagulant at D2 and terminates the anticoagulant priming operation.

Needle 22 is then inserted within the donor and whole blood is drawn from the donor and mixed with anticoagulant using pumps P101 and P102. The anticoagulated whole blood passes through valve V102, pump P102 and enters bowl 10 through port PT1. The blood is then separated into higher and low density components by rotating bowl 10 as described above. The low density component, plasma, is displaced from bowl 10 through port PT2. The plasma passes through line sensor 30 and valve V3. Approximately 200-250 ml of plasma is collected in plasma container 24. The separation process is terminated by stopping the rotation of bowl 10. Pump P102 returns the remaining components in bowl 10 to the donor through valve V102, filter chamber F3 and phlebotomy needle 22. Pump P101 draws saline solution from container 114 through valve V101 and filter F101 and mixes the saline solution with the blood components being returned to the donor at valve V102. The addition of saline solution to the remaining blood components allows the components to be returned to the donor at a rapid rate. Pumps P101 and P102 then draws anticoagulant from container 118 through valve V101, filter F101, valve V102 and port PT1 into bowl 10, thereby purging apparatus 110 of saline solution.

A second draw cycle from the donor is commenced in which another 200–250 ml of plasma is separated in bowl 10 and collected in plasma container 24. The rotation of bowl 10 is stopped, terminating the separation process and needle 22 is removed from the donor. The red cell contents of the bowl (approximately 250 ml) are drawn from bowl 10 by pump P102, and collected in red cell container 26 via valve V102. Pumps P101 and P102 draw additive solution from container 112 through valve 101, filter F101, valve V102 and port PT1 into bowl 10, thereby purging anticoagulant from apparatus 110. Pump P101 then draws additive from container 112 through valve V101, filter F101 and valve V102 into red cell container 26.

Alternatively, platelet container 44, line 42 and Valve V7 can be added to apparatus 40 for collecting platelets in the same manner performed by apparatus 8. Additionally, when collecting platelets, surge line 40 is added between plasma container 24 and valve V102.

While this invention has been particularly shown and described with references to the preferred embodiments thereof, it will be understood by those skilled in the art that various changes in form and details may be made therein without departing from the spirit and scope of the invention as defined by the appended claims.

We claim:

1. A method of automatically separating blood from a single donor via a single phlebotomy needle into constituent components comprising the steps:
    a) drawing a first collection of whole blood with said phlebotomy needle from said donor into a separation chamber;
    b) centrifugally separating a low density component from said first collection of whole blood from higher density components in the separation chamber, the higher density components from the first collection including white blood cells;
    c) displacing the low density component from the first collection to a first container for subsequent extracorporeal use;
    d) terminating the separation process in the chamber;
    e) returning the higher density components from the first collection remaining in the separation chamber to the donor via said phlebotomy needle, utilizing the returning higher density components with dilutent solution after exiting the separation chamber, the dilutent solution being Dumped into the higher density components at a rate high enough such that the higher density components can be returned to the donor at an elevated rate;
    f) drawing a second collection of whole blood from the same donor into the separation chamber;
    g) centrifugally separating a low density component from higher density components from said second collection of whole blood in the separation chamber;
    h) displacing the low density component from the second collection to the first container;
    i) terminating the separation process in the chamber;
    j) removing the phlebotomy needle from the donor;
    k) displacing the higher density components from the second collection remaining in the separation chamber to a second container for subsequent extracorporeal use, thereby collecting amounts of both higher density components and low density components in a relatively short period of time with increased yield and less inconvenience than if collected separately; and
    l) filtering white blood cells from the higher density components from the second collection before the higher density components enter the second container.

2. The method of separating blood of claim 1 further comprising the steps of:
    a) before drawing whole blood from the donor, priming a portion of a first line with saline solution, the first line being in fluid communication with the separation chamber;
    b) priming a portion of a second line with anticoagulant solution, the second line being in fluid communication with the phlebotomy needle; and
    c) equalizing pressure created during priming in the first and second lines.

3. The method of separating blood of claim 1 further comprising the steps:
    anticoagulating the withdrawn whole blood with anticoagulant after drawing the whole blood from the donor.

4. The method of separating blood of claim 1 further comprising the step of rejuvenating the higher density components held in the second container with additive solution.

5. The method of separating blood of claim 1 further comprising the step of rejuvenating the higher density components with additive solution before the higher density components enter the second container.

6. The method of separating blood of claim 1 in which the low density component from the first and second collections is plasma.

7. The method of separating blood of claim 1 in which the higher density components from the first and second collections further include red blood cells.

8. A method of automatically separating blood from a single donor via a single phlebotomy needle into constituent components in an apheresis apparatus comprising the steps:
    a) drawing a first collection of whole blood from said donor via said phlebotomy needle;
    b) anticoagulating the withdrawn whole blood with anticoagulant;
    c) forcing the anticoagulated whole blood into a separation chamber;
    d) centrifugally separating a low density component of said first collection of whole blood from higher density components in the separation chamber, the higher density components including white blood cells;
    e) displacing the low density component from the first collection to a first container for subsequent extracorporeal use;
    f) terminating the separation process in the chamber;
    g) returning the higher density components from the first collection remaining in the separation chamber to the donor via said phlebotomy needle, diluting the higher density components exiting the separation chamber with a dilutent solution pumped into the higher density components at a rate high enough such that the higher density components can be returned to the donor at an elevated rate and priming a first line with additive solution, the first line being in fluid communication with a second container;

h) drawing a second collection of whole blood from the donor into the separation chamber via said needle;

i) centrifugally separating a low density component from higher density components from said second collection of whole blood in the separation chamber;

j) displacing the low density component from the second collection to the first container;

k) terminating the separation process in the chamber;

l) removing the phlebotomy needle from the donor;

m) displacing the higher density components from the second collection remaining in the separation chamber to the second container for subsequent extracorporeal use, thereby collecting amounts of both higher density components and low density components in a relatively short period of time with increased yield and less inconvenience than if collected separately; and n) filtering white blood cells from the higher density components from the second collection before the higher density components enter the second container.

9. The method of separating blood of claim 8 further comprising the steps of:

a) priming the portion of a first line with diluent solution, prior to the first drawing step the first line being in fluid communication with the separation chamber;

b) priming a portion of a second line with anticoagulant solution, the second line for withdrawing whole blood from the donor; and c) equalizing pressure created during priming in the first and second lines.

10. The method of separating blood of claim 8 further comprising the step of rejuvenating the higher density components held in the second container with additive solution.

11. The method of separating blood of claim 8 further comprising the step of rejuvenating the higher density components with an additive solution before the higher density components enter the second container.

12. The method of separating blood of claim 8 in which the low density component from the first and second collections is plasma.

13. The method of separating blood of claim 8 in which the higher density components from the first and second collections further include red blood cells.

* * * * *